United States Patent
Bergh et al.

(10) Patent No.: US 6,485,419 B2
(45) Date of Patent: Nov. 26, 2002

(54) SYSTEMS AND METHODS FOR CONTROLLING PHYSICAL ACTIVITY DURING DIETING

(75) Inventors: Cecilia Bergh; Per Södersten, both of Stockholm (SE)

(73) Assignee: Mandometer AB (SE)

( * ) Notice: Subject to any disclaimer, the term of this patent is extended or adjusted under 35 U.S.C. 154(b) by 0 days.

(21) Appl. No.: 09/943,493

(22) Filed: Aug. 30, 2001

(65) Prior Publication Data
US 2002/0082481 A1 Jun. 27, 2002

(30) Foreign Application Priority Data
Dec. 19, 2000 (SE) .................................. 0004710

(51) Int. Cl.[7] ................................. A61B 5/00
(52) U.S. Cl. ....................... 600/300; 128/921
(58) Field of Search ................ 600/300, 301; 128/921; 126/204, 205; 607/96, 98, 103, 104; 177/245, 264; 434/127

(56) References Cited

U.S. PATENT DOCUMENTS

| | | | | |
|---|---|---|---|---|
| 4,718,429 A | * | 1/1988 | Smidt | 607/104 |
| 5,018,521 A | * | 5/1991 | Campbell | 607/98 |
| 5,817,006 A | * | 10/1998 | Bergh et al. | 600/300 |

* cited by examiner

*Primary Examiner*—Kevin Shaver
*Assistant Examiner*—David McCrosky
(74) *Attorney, Agent, or Firm*—Dean W. Russell; Kilpatrick Stockton LLP

(57) ABSTRACT

The invention relates to a system and a method for controlling physical activity while dieting. A computer (14) with a screen (20) and a connected scale (24) providing a plate (26) used for intake of food by a user (28) is used to determine a best level of dieting for the user (28). The dieting level is correlated with a level for warming or cooling the body of a user. This provides that additional physical activity for a certain level of dieting is prevented and raised, respectively, in order to achieve a best possible and healthy diet mode.

24 Claims, 1 Drawing Sheet

SYSTEMS AND METHODS FOR CONTROLLING PHYSICAL ACTIVITY DURING DIETING

TECHNICAL FIELD

The present invention pertains to a system and a method for controlling physical activity during dieting in order to achieve a good mode of dieting.

BACKGROUND ART

There are lots of people in our society today who are in need of an aid for dieting in a controlled manner. These are, for example, athletes, overweight and obese persons and others who have to care about a controlled way of eating. A specific problem while dieting relates to a correct or suitable physical activity in combination with the dieting. People tend to overdo with more physical activity than required for a specific level of dieting.

A problem is that there are plenty of methods and devices on the market to keep a diet, such as athletic training equipment, drugs, designed food for dieting, associations for dieting etc. If a person dieting shall be able to succeed in doing so and achieve an intended goal she/he should be supervised by people experienced in this art, for example, experts on nutrition, doctors and the like. But it is also important that experts have a reliable aid to make use of when supervising during a time period of dieting. Also, persons under diet should have an aid that they can rely on when they are without supervision from specific experts in the field.

It is known that a controlled diet gives an as good result as the combination of physical activity and dieting, at least for people with ordinary needs of physical activity, i.e., non athletes, who should combine dieting with ordinary daily activities such as a daily walk. Athletes on the other hand do have to take the same care of their body when preparing for major sporting events, whereby they have to be careful with their food intake in correlation with their training effort.

There are unfortunately also lethal diseases related to a wrong dieting and such related to unhealthy dieting, such as anorexia, bulimia, and disorders related to digestion or gastrointestinal discomfort. Therefore, people at risk and/or their doctors should appreciate an aid for a good and healthy dieting.

U.S. Pat. No. 5,817,006 by Bergh and Södersten, hereby incorporated in the description of the present invention, is based on the development of the measurement of eating rate, whereby different rates of ingestion correspond to a biologically determined degree of satiety. Eating rate is measured utilizing the variables (weight of food, time). For the quantification of satiety the interval scale of Borg is used. The invention makes use of reference standards (standard curves or curves of normality), obtained from research on a population of individuals. These curves reflect the average rate of ingestion that has been found statistically significant through the investigation of groups, differing in, for example, age and weight, within the population of men and women. The interval scale of Borg is used to record satiety.

One aim of the invention according to the U.S. Pat. No. 5,817,006 by Bergh and Södersten, is to develop a measuring device that allows, among others, obese people to gain access to a method for weight control. Overweight and obesity is a major health problem, and the overweight, therefore, have an obvious interest in such a device.

Furthermore, the control of body weight and ingestive behaviour is of considerable importance to athletes and those engaged in sports. A method for the control of body weight and eating behaviour is also needed within clinical medicine to care for patients suffering from anorexia, bulimia and gastrointestinal discomfort, that is to say disorders related to the intake of food. Use of the present method and device is likely to be of importance to those within the general public who are at risk to develop disorders of body weight control.

A device, according to the U.S. Pat. No. 5,817,006 by Bergh and Södersten, mentioned provides assistance in the control of body weight for the individual with a possibility to control eating behaviour and the perception of satiety and, therefore, a method to control body weight. This is accomplished by the display of the reference standards on a monitor/screen. The reference standards for eating behaviour and satiety as a function of eating rate are derived from biologically based mean values obtained through research on samples of individuals from the general population. Using this device, the individual is in a position to adapt her/his eating behaviour and perception of satiety to what, by definition, is normal through the selection of the proper reference values and by adapting her/his rate of ingestion to the reference value displayed on a medium, for example a monitor, in real time. The rate of ingestion of the individual is displayed simultaneously with the reference standard and the two are to overlap.

Persons participating in the development of the invention and displaying deviations from the reference standards with respect to eating behaviour and perception of satiety have considered themselves unable or ignorant as to how to eat and how to feel satiated.

However the U.S. Pat. No. 5,817,006 by Bergh and Södersten, does not teach how to correlate an efficient amount of physical activity to a certain level of dieting. Especially there is no teaching of how to avoid unnecessary physical activity in combination with the eating training.

SUMMARY OF THE DISCLOSED INVENTION

It is an aim of the present invention to provide a system and a method to be used for controlling the amount of physical activity when dieting. In order to accomplish an aid for this, the present invention makes use of the teachings in the above mentioned U.S. Pat. No. 5,817,006 by Bergh and Södersten, by combining it with the use of heating and/or cooling means warming or cooling a human body. Thereby the invention makes use of the knowledge of applying heat to a body in order to reduce physical activity. People who are freezing are moving their limbs in order to warm the body with the energy they are consuming during the movement. Hence, the vice versa should apply, i.e., heating the body from an external heat source such as a fire, thus being able to ignore freezing without additional physical activity.

Hence there is a close relation between dieting, which reduces the source of energy to be consumed, and the providing of heat to a dieting person's body.

In general the following rule prevails throughout the present invention. For an obese person the body temperature should be lowered and the physical activity should be raised in order to lose weight, and for a person with low weight, the body temperature should be raised and physical activity should be reduced in order to gain or keep weight. Of course there are weights between obese and low weight where a fairly low weight person should lose weight.

The present invention thus proposes a system for controlling physical activity during dieting. It comprises:

a scale with a plate for food intake situated on it;

a computer with a screen, and an input device connected to the scale which calculates and stores the weight loss of the food when eating from the plate, whereby a dieting user eating from the plate should eat in accordance with a rating illustrated on the screen in order to receive a correct response of food intake for a determined level of dieting; and a heating or cooling means providing a determined level of heat to the body of the user for the level of dieting, thus adapting physical body activity to a level corresponding to the dieting level, whereby physical activity is being correlated to the level of dieting.

One embodiment of the system of the present invention provides that a determined level of dieting is correlated to a minimum degree of heating temperature or a maximum degree of cooling temperature applied to the body from the means for heating or cooling.

Another embodiment provides that the duration of applied heat or cooling is correlated with the determined level of dieting.

A further embodiment provides that the level of dieting is determined from a self-rating questionnaire displayed on the screen with at least one scale relating to a body condition of a user.

A still further embodiment provides that a filled out questionnaire is compared with a questionnaire manual stored in the computer providing reference values for body conditions for different body parameters, in order to determine a best level of dieting for a user.

Yet another embodiment provides that a heating and/or cooling means is controlled by the computer.

Yet still another embodiment provides that the control is regulated in accordance with body condition parameters stored in the computer for the user.

In one embodiment the heating means is an electrically heated body-wear.

In another embodiment the heating means is a heated room.

A further embodiment provides that a heating means is an electronically heated blanket, cushion or other bed-wear.

A still further embodiment of the invention provides that a user updates a diary in the computer for a time period of dieting, thus entering at least body condition parameters. Additionally, the body condition parameters are used by a computer dieting means to determine a next level for dieting.

Further the present invention sets forth a method for controlling physical activity during dieting, thereby comprising the steps of:

using a scale with a plate for food intake situated on it;

using a computer with a screen, and an input device connected to the scale which calculates and stores the weight loss of the food when eating from the plate, whereby a dieting user eating from the plate should eat in accordance with a rating illustrated on the screen in order to receive a correct response of food intake for a determined level of dieting; and using a heating or cooling means providing a determined level of heat to the body of the user for the level of dieting, thus adapting physical body activity to a level corresponding to the dieting level, whereby physical activity is being correlated to the level of dieting.

It is appreciated that the embodiments of the system are provided with the method of the present invention in accordance with the attached set of method sub-claims.

BRIEF DESCRIPTION OF THE DRAWINGS

Henceforth reference is had to the attached drawings in context of the accompanying description for a better understanding of the present invention with its embodiments and given examples, wherein.

DETAILED DESCRIPTION OF PREFERRED EMBODIMENTS

The present invention provides a new and inventive system and method for controlling physical activity during dieting in order to achieve a good mode of dieting. Hereby it makes use of the knowledge of applying heat to a body in order to reduce physical activity. People who are freezing are moving their limbs in order to warm the body with the energy they are consuming during the movement. Hence the vice versa should apply, i.e., heating the body from an external heat source such as a fire, thus being able to ignore coldness without using additional physical activity. This knowledge is provided together with the teaching of the U.S. Pat. No. 5,817,006 by Bergh and Södersten.

As mentioned, the following rule prevails throughout the present invention.

Rule: For an obese person the body temperature should be lowered and the physical activity should be raised in order to lose weight, and for a person with low weight, the body temperature should be raised and physical activity should be reduced in order to gain or keep weight.

Figure 1:
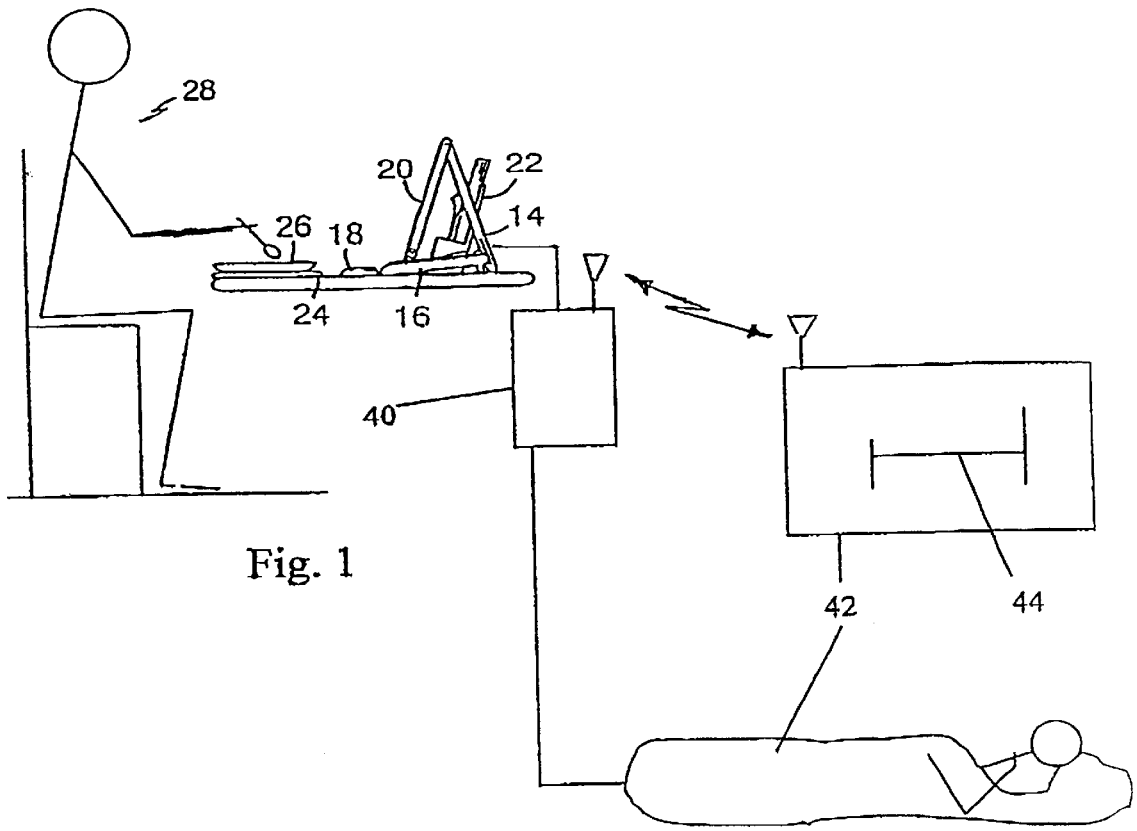
FIG. 1 illustrates a system for controlling physical activity during dieting in accordance with one embodiment of the present invention.

FIG. 1 shows a measuring device with a first means, herein a computing system, with a computer 14 and a peripheral equipment, including a key panel 16, a mouse 18, a track ball or a pointing device, a monitor/screen 20 and a printer 22. The scale 24 in this embodiment is comprised in the measuring device. Peripheral equipment, apart from being mediated via a cable, may be mediated wireless by means of known technology (not shown), for example infrared, radio or the like technology. The scale 24, preferably a digital one although others are conceivable, need not be connected to the computer by any special adaptation. An analogue scale demands an adaptation device for sampling, quantification and analogue/digital conversion.

Henceforth, the examples and embodiments of the present invention are described as using heating means 42 to control physical activity, but it should be appreciated that cooling means are as likely to be provided. This in the context of obese persons who need to be cooled in order to raise their amount of physical activity while dieting. A heating and cooling device 42 to use both to train obese and low weight persons could thus be an air conditioner (AC), heat exchanger or the like. An obese person could be exposed to a determined temperature level through an AC in a room 42 controlled by the heat controller 40, and use provided training equipment such as weightlifting gear, treadmill, tread conveyer belt, or else any common training equipment. The training equipment could also be provided in rooms 42 when applying heat to low weight persons for their determined physical activity.

In one embodiment of the present invention an I/O port of the computer 14 is connected to a control device 40 for controlling heat radiation and time duration for it to an heating means 42, here illustrated as a sleeping-bag 42 or a room 42 with a bed 44 for resting. The heating means could alternatively be electrically heated body-wear including foot-wear such as shoes, stockings, or electrically heated bed-wear such as blankets, mattresses etc.

Protocols and other software by the present invention do not demand new technology of computing or communication. The required technology of the present invention is known to those skilled in the art of computer technology and need not be elaborated here. Any computing system, that is available on the market, e.g. PC, Macintosh, portable computers or other, can be adapted. However, the system and the method to utilize the invention and the measuring device together with a heating or cooling means 42 to control physical activity during dieting are inventive features of the present invention.

Utilization of the measuring device requires a means 26 for the presentation of food, from which the user and measuring object 28, for example, an athlete preparing for a major athletic competition, ingests food. It is possible for an athlete supervisor to participate as an observer. This means 26 is, most suitably, a common piece of household ware, such as a plate, a bowl or a serving plate.

To carry out a test with the measuring device the program that controls the measurement is started, for example via the mouse 18, the steering ball or the key panel 16. It is also possible to start measuring when the plate 26 is placed on the scale 24. Thereafter, the above described method is started to complete a test. If placement of the plate 26 does not initiate the measurement, the user 28 places the plate 26 on the scale, and, thereafter, starts the measurement and the selection of reference standards 30, solid line of eating behaviour in FIG. 2 via the mouse.

Figure 2:
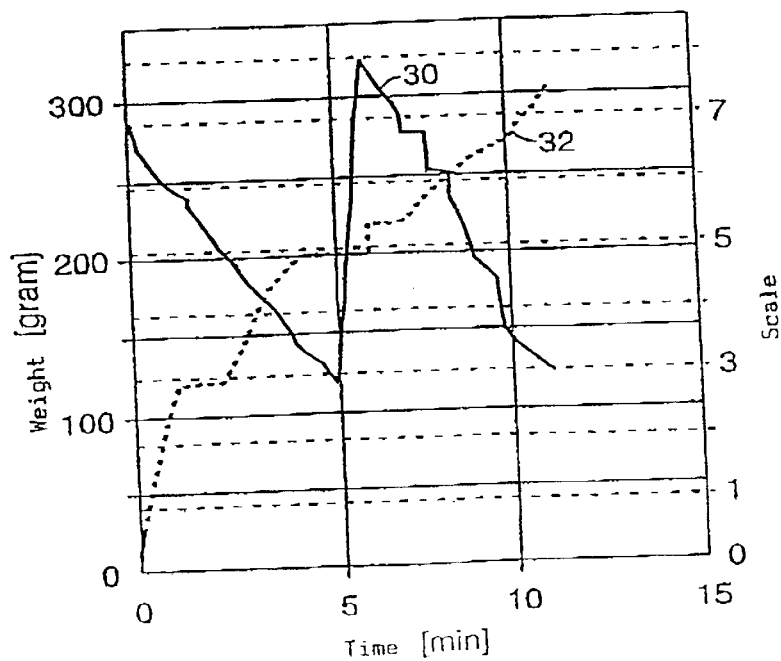
FIG. 2 illustrates a display on a computer screen with a standard curve of reference comprising a scale of satiety and an overlapping curve with actual measures of eating rate from an object of measurement used in one embodiment of the present invention.

FIG. 2 illustrates a display on a computer screen with a standard curve of reference comprising a scale of satiety and an overlapping curve with actual measures of eating rate from an object of measurement used in one embodiment of the present invention. It hereby illustrates a display on a computer screen with a standard curve of reference comprising a scale of satiety and an overlapping curve with actual measures of eating rate from an object of measurement used in one embodiment of the present invention.

The interval scale of satiety included in FIG. 2 shows 8 intervals for satiety rating. The satiety is recorded at specified time points of the curve of eating rate. The width of the intervals is dependent of the biologically based perception of satiety in relation to the proper reference standard. As mentioned satiety is determined by the rate of eating and mediated by the biological factors mentioned above.

A period of measurement can also be initiated via the key panel 16, but normally this is done only when retrieving data and when updating programs. The standard of reference will become visible on a picture medium that is connected to the device, in this case the monitor/screen 20 of the computing system. If the user or the observer wants the method to run "blind" it might be feasible not to display the standard to the user but store it in the computer for printout for example via a printer 22 or delayed printout and the associated evaluation of the obtained rates of ingestion in relation to the standard of reference or other evaluations, such as evaluation of rating of satiety and statistical analyses. A blind measurement can also be accomplished by turning the monitor 20 away from the measuring object and permit only the observer to follow the method. After the start of a period of measurement and placement of the plate 26 on the scale, the food, which is selected according to the reference standard, is placed on the plate, stabilization of the scale is allowed for some seconds and the user 28 starts eating. The rate of ingestion 32, the dotted line in FIG. 2, is then displayed over or overlapping the standard of reference on the monitor 20 thus making comparison in real time immediately possible and allowing measures, such as modifying the rate of ingestion, for adapting to the reference standard to be taken. Addition of food is made with reference to the standard 30, for example by clicking the mouse at regular time intervals which results in a display of information on how much food should be provided. The method is terminated preferably by lifting the plate 26 from the scale 24. The results of the measurement are stored internally in one or several files, for later use, in the central unit 14 or in an external storage medium via one of the communication ports of the central unit.

Hence, the present invention provides a system for controlling physical activity during dieting. It utilizes a scale 24 with a plate 26 for food intake situated on it. A computer 14 with a screen 20, and an input device 16, 18 connected to the scale 24, which calculates and stores the weight loss of the food on the plate 26 when eating from it.

A dieting user 28 eating from the plate should eat in accordance with a rating illustrated on the screen 20, see FIG. 2, in order to receive a correct response of food intake for a determined level of dieting.

An inventive aspect of the present invention combines the eating with a heating means 42, here an electrically heated room 42 with a rest bed 44 or an electrically heated sleeping-bag 42. It provides a determined level of heat to the body of the user 28 for a determined level of dieting through a thermostat and a timer 40. The thermostat regulates the heating temperature and the timer the duration of a heating cycle, thus adapting physical body activity to a level corresponding to a determined dieting level. This allows that physical activity is being correlated to a desired level of dieting.

The period of warming the body of a user preferably begins when eating is finished, whereby the user can lie down on the bed 44 in the heated room 42 for rest during a time period determined for the person's 28 specific level of dieting. This time period can in one embodiment be determined by the computer 14, computing statistics for ordinary body parameters in a general public in correlation with that person's body parameters such as BMI.

In another embodiment the period of warming the body could start simultaneously with the start of eating, whereby the user can bear electrically heated body-wears such as socking, jacket etc.

It is appreciated that the heating means of the present invention either can be controlled by the computer 14 through the heating control means 40, by taking into account eating speed, satiety, body parameters of a user 28 such as Body Mass Index (BMI) and others known to a person skilled in the art The heating control means 40 control heat radiation in the heating means through cable or through wire-less techniques such as radio-, infrared-communication, ultra-sound-communication or other like techniques through receivers and/or transmitters as indicated by the antennas and the flash arrow in FIG. 1. Another option is to let the computer compute a level of heating and/or time duration and display it on the screen 20 for manual control of the heating device 42. A still further alternative for the amount of heating radiation and/or duration is that users 28 themselves can decide how much heat to apply and/or the time duration of it.

A determined level of dieting is in one embodiment of the invention correlated to a minimum degree of heating temperature (maximum degree of cooling temperature for obese persons) applied to the body of a user 28 from the means 42 for heating or cooling. The time duration of applied heat can be correlated with the determined level of dieting, wherein the level of dieting is determined from a self-rating questionnaire displayed on the screen 20 with a scale relating to a body condition of a user. Such a body condition could be satiety, weight, BMI etc. To protect dieting users from mal-use of the system according to the invention, a filled out questionnaire is compared with a questionnaire manual. This manual is stored in the computer and provides reference values for body conditions for different body parameters, to determine a best determined level of dieting for a user body in correspondence with prevailing body conditions. By comparing user entered data with manual data heavy dieting can be prevented or at least the computer could put out a warning message.

A further embodiment of the present invention provides that a user updates a diary in the computer memory for a period of dieting, thus entering at least body condition parameters. This gives the user a history of the dieting period and how she/he felt during a specific level of dieting. Advantageously this body condition parameters can be used by a computer statistic software means to determine a next level of dieting.

While the system and method shown or described has been characterized as being preferred it will be obvious that various changes and modifications may be made therein without departing from the scope of the invention as defined in the attached set of claims.

We claim:

1. A system for controlling physical activity during dieting, comprising:
   a scale (24) with a plate (26) for food intake situated on it;
   a computer (14) with a screen (20), and an input device (16, 18) connected to said scale (24) which calculates and stores the weight loss of said food when eating from said plate (26), whereby a dieting user (28) eating from said plate should eat in accordance with a rating (30) illustrated on said screen (20) in order to receive a correct response of food intake for a determined level of dieting; and
   a heating or cooling means (42) providing a determined level of heat to the body of said user (28) for said level of dieting, thus adapting physical body activity to a level corresponding to said dieting level, whereby physical activity is being correlated to said level of dieting.

2. A system according to claim 1, wherein said determined level of dieting is correlated to a minimum degree of heating temperature or a maximum degree of cooling applied to said body (28) from said means for heating (42) or cooling.

3. A system according to claim 1, wherein the duration of applied heat is correlated with said determined level of dieting.

4. A system according to claim 1, wherein said level of dieting is determined from a self-rating questionnaire displayed on said screen with at least one scale relating to a body condition of a user.

5. A system according to claim 4, wherein a filled out questionnaire is compared with a questionnaire manual stored in said computer providing reference values for body conditions for different body parameters, in order to determine a best determined level of dieting for the user.

6. A system according to claim 1, wherein said heating means (42) or cooling means are controlled (40) by said computer (14).

7. A system according to claim 6, wherein said control (40) is regulated in accordance with body condition parameters stored in said computer (14) for said user (28).

8. A system according to claim 1, wherein said heating means (42) is an electrically heated body-wear.

9. A system according to claim 1, wherein said heating means is a heated room (42).

10. A system according to claim 1, wherein said heating means (42) is an electronically heated blanket, cushion or other bed-wear.

11. A system according to claim 1, wherein a user updates a diary in said computer (14) for a period of dieting, thus entering at least body condition parameters.

12. A system according to claim 11, wherein said body condition parameters are used by a computer dieting means to determine a next level for dieting.

13. A method for controlling physical activity during dieting, comprising the steps of:
   using a scale (24) with a plate (26) for food intake situated on it;
   using a computer (14) with a screen (20), and an input device (16, 18) connected to said scale (24) which calculates and stores the weight loss of said food when eating from said plate (26), whereby a dieting user (28) eating from said plate (26) should eat in accordance with a rating (30) illustrated on said screen (20) in order to receive a correct response of food intake for a determined level of dieting; and
   using a heating or cooling means (42) providing a determined level of heat to the body of said user (28) for said level of dieting, thus adapting physical body activity to a level corresponding to said dieting level, whereby physical activity is being correlated to said level of dieting.

14. A method according to claim 13, wherein said determined level of dieting is correlated to a minimum degree of heating temperature or a maximum degree of cooling applied to said body from said means for heating (42).

15. A method according to claim 13, wherein the duration of applied heat is correlated with said determined level of dieting.

16. A method according to claim 13, wherein said level of dieting is determined from a self-rating questionnaire displayed on said screen (20) with at least one scale relating to a body condition of a user (28).

17. A method according to claim 16, wherein a filled out questionnaire is compared with a questionnaire manual stored in said computer (14) providing reference values for body conditions for different body parameters, in order to determine a best determined level of dieting for a user (28).

18. A method according to claim 13, wherein said heating or cooling means (42) are controlled (40) by said computer (14).

19. A method according to claim 18, wherein said control (40) is regulated in accordance with body condition parameters stored in said computer (14) for said user (28).

20. A method according to claim 13, wherein said heating means (42) is an electrically heated body-wear.

21. A method according to claim 13, wherein said heating means (42) is a heated room.

22. A method according to claim 13, wherein said heating means (42) is an electrically heated blanket, cushion or other bed-wear.

23. A method according to claim 13, wherein a user (28) updates a diary in said computer (14) for a period of dieting, thus entering at least body condition parameters.

24. A method according to claim 23, wherein said body condition parameters are used by a computer dieting means to determine a next level of dieting.

* * * * *